US008475787B2

(12) United States Patent
Harper

(10) Patent No.: US 8,475,787 B2
(45) Date of Patent: Jul. 2, 2013

(54) BENEFICIAL EFFECTS OF BACTERIOPHAGE TREATMENTS

(75) Inventor: David Harper, Greenfield (GB)

(73) Assignee: Bio-Control Limited, Nottingham (GB)

( * ) Notice: Subject to any disclaimer, the term of this patent is extended or adjusted under 35 U.S.C. 154(b) by 379 days.

(21) Appl. No.: 12/529,876

(22) PCT Filed: Mar. 7, 2008

(86) PCT No.: PCT/GB2008/050162
§ 371 (c)(1),
(2), (4) Date: Dec. 22, 2009

(87) PCT Pub. No.: WO2008/110840
PCT Pub. Date: Sep. 18, 2008

(65) Prior Publication Data
US 2010/0104538 A1   Apr. 29, 2010

(30) Foreign Application Priority Data

Mar. 9, 2007 (GB) .................................. 0704553.7

(51) Int. Cl.
*A01N 63/00* (2006.01)
*A61K 39/108* (2006.01)
*A61K 39/00* (2006.01)
*A61K 45/00* (2006.01)
*A61K 47/00* (2006.01)

(52) U.S. Cl.
USPC .................... 424/93.6; 424/260.1; 424/184.1; 424/278.1; 424/93.47

(58) Field of Classification Search
None
See application file for complete search history.

(56) References Cited

U.S. PATENT DOCUMENTS

| | | | |
|---|---|---|---|
| 4,678,750 | A | 7/1987 | Vandenbergh et al. |
| 4,828,999 | A | 5/1989 | Jackson |
| 5,242,902 | A | 9/1993 | Murphy et al. |
| 5,582,825 | A | 12/1996 | Sakaguchi et al. |
| 5,641,497 | A | 6/1997 | Bevins et al. |
| 6,121,036 | A * | 9/2000 | Ghanbari et al. .......... 435/235.1 |
| 6,161,036 | A | 12/2000 | Matsumura et al. |
| 6,461,608 | B1 | 10/2002 | Averback et al. |
| 6,861,230 | B1 * | 3/2005 | Murphy et al. .............. 435/7.32 |
| 7,758,856 | B2 | 7/2010 | Hughes et al. |
| 7,807,149 | B2 | 10/2010 | Soothill et al. |
| 8,388,946 | B2 | 3/2013 | Soothill et al. |
| 2002/0001590 | A1 | 1/2002 | Kelly et al. |
| 2002/0037260 | A1 | 3/2002 | Budny et al. |
| 2002/0090356 | A1 | 7/2002 | Waddell et al. |
| 2004/0208853 | A1 | 10/2004 | Sulakvelidze et al. |
| 2004/0247569 | A1 | 12/2004 | Morris et al. |
| 2005/0152818 | A1 | 7/2005 | Botvinnik et al. |
| 2006/0140911 | A1 | 6/2006 | Sharp et al. |
| 2010/0104538 | A1 | 4/2010 | Harper |
| 2011/0020290 | A1 * | 1/2011 | Soothill et al. ............... 424/93.6 |
| 2012/0114611 | A1 | 5/2012 | Soothill et al. |

FOREIGN PATENT DOCUMENTS

| | | |
|---|---|---|
| JP | 2006-520908 | 9/2006 |
| RU | 2 186 574 C1 | 1/2001 |
| SU | 1472500 A1 | 4/1989 |
| WO | WO 89/11291 | 11/1989 |
| WO | WO 94/21672 | 9/1994 |
| WO | WO 95/32287 | 11/1995 |
| WO | WO 97/39111 | * 10/1997 |
| WO | WO 98/47521 | 10/1998 |
| WO | WO 01/50866 A2 | 7/2001 |
| WO | WO 02/07742 A2 | 1/2002 |
| WO | WO 03/008564 A2 | 1/2003 |
| WO | WO 2004/062677 A1 | 7/2004 |
| WO | WO 2005/009451 | 2/2005 |
| WO | WO 2005/009451 A1 * | 2/2005 |

OTHER PUBLICATIONS

Hatch et al., "Alginate Lyase Promotes Diffusion of Aminoglycosides through the Extracellular Polysaccharide of Mucoid *Pseudomgnas aeruginosa*," Antimicrobial Agents and Chemotherapy, pp. 974-977, (1998), 42(4).
Mai et al., "Inhibition of Adherence of Mucoid *Pseudomonas aeruginosa* by Alginase, Specific Monoclonal Antibodies, and Antibiotics," Infection and Immunity, pp. 4338-4343, (1993), 61(10).
Hariharan, H. et al., "Minimal inhibitory concentrations of twenty antimicrobial agents to animal pathogens", Canadian Journal of Comparative Medicine, vol. 38, No. 4, pp. 437-442, (1974).
Parment, P.A. et al., "The efficacy of soft contact lens disinfection solutions against serratia marcescens and *Pseudomonas aueruginosa*", Acta Opthalmologica Scandinavica, vol. 74, No. 3, pp. 235-237, (1996).
Lewis, K. "Persister cells, dormancy and infectious disease", Nature Reviews Microbiology, vol. 5, pp. 48-56, (2007).
Spoering, A.L. et al., "Biofilms and planktonic cells of *Pseudomonas aeruginosa* have similar resistance to killing by antimicrobials", Journal of Bacteriology, vol. 183, No. 23, pp. 6746-6751, (2001).
U.S. Appl. No. 13/333,684, Aug. 30, 2012.
Corbin et al., "Bacteriophage T4 multiplication in a glucose-limited *Escherichia coli* biofilm," Can. J. Microbiol., vol. 47, pp. 680-684, (2001).
Doolittle et al., "Lytic infection of *Escherichia coli* biofilms by bacteriophage T4," Can. J. Microbiol., vol. 41, pp. 12-18, (1995).
Doolittle et al., "Tracing the interaction of bacteriophage with bacterial biofilms using fluorescent and chromogenic probes," Journal of Industrial Microbiology, vol. 16, pp. 331-341, (1996).

(Continued)

*Primary Examiner* — Vanessa L Ford
*Assistant Examiner* — Lakia Tongue
(74) *Attorney, Agent, or Firm* — Evan Law Group LLC

(57) ABSTRACT

The invention relates to use of one or more bacteriophages in vivo in a human or animal in order to induce sensitivity to chemical antibiotics in bacterial cells, where such susceptibility is heritable, independent of continuing bacteriophage metabolism within those cells, and does not relate to the destruction of a biofilm to induce such sensitivity.

16 Claims, No Drawings

OTHER PUBLICATIONS

Hancock et al., "Peptide Antibiotics," Antimicrobial Agents and Chemotherapy, vol. 43, pp. 1317-1323, (1999).
Hanlon et al., "Reduction in Exopolysaccharide Viscosity as an Aid to Bacteriophage Penetration through *Pseudomonas aeruginosa* Biofilms," Appl. Environ. Microbiol., vol. 67, pp. 2746-2753, (2001).
Hatch et al., "Alginate Lyase Promotes Diffusion of Aminoglycosides through the Extracellular Polysaccharide of Mucoid *Pseudomonas aeruginosa*," Antimicrob. Agents Chemother., vol. 42, pp. 974-977, (1998).
Hughes et al., "Biofilms susceptibility to bacteriophage attack: the role of phage-borne polysaccharide depolymerase," Microbiology, vol. 144, pp. 3039-3047, (1998).
Hughes et al., "Biofilms, Bacteriophage Interactions and Bacteriophage Therapy," BioLine, pp. 325-331, (2001).
Mah et al., "Mechanisms of biofilm resistance to antimicrobial agents," Trends in Microbiology, vol. 9, No. 1, pp. 34-39, (2001).
Merril et al., "The prospect for bacteriophage therapy in Western medicine," Nature Reviews: Drug Discovery, vol. 2, pp. 489-497, (2003).
Nickel et al., "Tobramycin Resistance of *Pseudomonas aeruginosa* Cells Growing as a Biofilm on Urinary Catheter Material," Antimicrobial Agents and Chemotherapy, vol. 27, No. 4, pp. 619-624, (1985).
Roy et al., "Biological Inactivation of Adhering *Listeria monocytogenes* by Listeriaphages and a Quaternary Ammonium Compound," Appl. Environ. Microbiol., vol. 59, No. 9, pp. 2914-2917, (1993).
Soothill, "Bacteriophage prevents destruction of skin grafts by *Pseudomonas aeruginosa*," Burns, vol. 20, No. 3, pp. 209-211, (1994).
Stewart et al., "Antibiotic resistance of bacteria in biofilms," The Lancet, vol. 358, pp. 135-138, (2001).
Sutherland et al., "Polysaccharides in Biofilms and Their Interactions with Phage and Antimicrobials," BioLine, pp. 179-187, (1999).
Sutherland, "Polysaccharases for microbial exopolysaccharides," Carbohydrate Polymers, vol. 38, pp. 319-328, (1999).
Tait et al., "The Efficacy of Bacteriophage as a Method of Biofilm Eradication," Biofouling, vol. 18, No. 4, pp. 305-311, (2002).
Wood et al., "Susceptibility of *Staphylococcus epidermis* Biofilm in CSF Shunts to Bacteriophage Attack," Eur. J. Pediatr. Surg., vol. 11, Suppl. 1, pp. S56-S57, (2001).
UK Search Report for GB 0300597.2, dated Jun. 30, 2003, 1 page.
Barrow et al., "Use of Lytic Bacteriophage for Control of Experimental *Escherichia coli* Septicemia and Meningitis in Chickens and Calves," Clin. Diagn. Immunol., vol. 5, No. 3, pp. 294-298, (1998).
Biswas et al., "Bacteriophage Therapy Rescues Mice Bacteremic from a Clinical Isolate of Vancomycin-Resistant *Enterococcus faecium*," Infect. Imm., vol. 70, No. 1, pp. 204-210, (2002).
Kitamikado et al., "Method Designed to Detect Alginate-Degrading Bacteria," Appl. Environ. Microbiol., vol. 56, No. 9, pp. 2939-2940, (1990).
Smith et al., "Effectiveness of Phages in Treating Experimental *Escherichia coli* Diarrhoea in Calves, Piglets and Lambs," J. Gen. Microbiol., vol. 129, pp. 2659-2675, (1983).
Smith et al., "The Control of Experimental *Escherichia coli* Diarrhoea in Calves by Means of Bacteriophages," J. Gen. Microbiol., vol. 133, pp. 1111-1126, (1987).
Weiner et al., "Structure, function and immunochemistry of bacterial exopolysaccharides," J. Ind. Microbial., vol. 15, pp. 339-346, (1995).
Nairn, "Solutions, Emulsions, Suspensions and Extracts," Chapter 86 in Remington: The science and practice of pharmacy, vol. II, pp. 1495-1523, (1996).
Lee et al., "Characterization of Bacteriophage gh-1 for *Pseudomonas putida*," J. Bacteriol, vol. 92, No. 6, pp. 1821-1827, (1966).
Slopek et al., "Results of Bacteriophage Treatment of Suppurative Bacterial Infections III. Detailed Evaluation of the Results Obtained in Further 150 Cases," Archivum Immunologiae Et. Therapiae Experimentalis, vol. 32, pp. 317-335, (1984).
Carlton, "Phage Therapy: Past History and Future Prospects," Archivum Immunologiae Et Therapiae Experimentalis, vol. 47, pp. 267-274, (1999).
Kudva et al., "Biocontrol of *Escherichia coli* O157 with O157-Specific Bacteriophages," Appl. Environ. Micro., vol. 65, No. 9, pp. 3767-3773, (1999).
UK Search Report for GB 0317240.0, dated Oct. 15, 2003, 2 pages.
Wright et al., "A controlled clinical trial of a therapeutic bacteriophage preparation in chronic otitis due to antibiotic-resistant *Pseudomonas aeruginosa*; a preliminary report of efficacy," Clin. Otolaryngol., vol. 34, pp. 349-357, (2009).
Marza et al., "Multiplication of therapeutically administered bacteriophages in *Pseudomonas aeruginosa* infected patients," Elsevier Burns, vol. 32, pp. 644-646, (2006).
Donlan, "Biofilms: Microbial Life in Surfaces," Emerging Infectious Diseases, vol. 8, No. 9, pp. 881-890, (2002).
Chen et al., "*Pseudomonas* Infection," http://www emedicine.com/PED/topic2701.html, 37 pages, (2002).
Qarah et al., "*Pseudomonas aeruginosa* Infections," http://www.emedicine.com/MED/topic1943.html, 22 pages, (2001).
Friedman et al., "Genes involved in matrix formation in *Pseudomonas aeruginosa* PA14 biofilms," Molecular Microbiology, vol. 51, pp. 675-690, (2004).
Henwood et al., "Antimicrobial susceptibility of *Pseudomonas aeruginosa*: results of a UK survey and evaluation of the British Society for Antimicrobial Chemotherapy disc susceptibility test," Journal of Antimicrobial Chemotherapy, vol. 47, pp. 789-799, (2001).
Gerberding et al., "National Nosocomial Infections Surveillance (NNIS) System Report, Data Summary from Jan. 1992-Jun. 2001, Issued Aug. 2001," American Journal of Infection Control, vol. 29, pp. 404-421, (2001).
Heinkoff et al., "Amino acid substitution matrices from protein blocks," Proc. Natl. Acad. Sci., vol. 89, pp. 10915-10919, (1992).
Karlin et al., "Applications and statistics for multiple high-scoring segments in molecular sequences," Proc. Natl. Acad. Sci., vol. 90, pp. 5873-5877, (1993).
Rahim et al., "Linezolid-Resistant, Vancomycin-Resistant *Enterococcus faecium* Infection in Patients without Prior Exposure to Linezolid," Clin. Infect. Dis., vol. 36, pp. E146-E148, (2003).
Devereux et al., "A comprehensive set of sequence analysis programs for the VAX," Nucleic Acids Research, vol. 12, No. 1, pp. 387-395, (1984).
Mutnick et al., "Linezolid Resitance Since 2001: SENTRY Antimicrobial Surveillance Program," The Annals of Pharmacotherapy, vol. 37, pp. 769-774, (2003).
Fletcher et al., "Biofilms," Encyclopedia of Life Sciences, Nature Publishing, London, Clin. Pharmacokinet, 7 pages, (2001).
Iglewski, "Pseudomonas," Medical Microbiology 4th edition, S. Baron (ed). University of Texas; http://www.ncbi.nlm.nih.gov/bookshelf/br.fcgi?book=mmed&part=A1503, pp. 1-8, (1996).
Hoiby. "Pseudomonas in cystic fibrosis: past, present, future," European Cystic Fibrosis Society Joseph Levy Memorial Lecture; 38 pages, (1998).
Mah et al., "A genetic basis for *Pseudomonas aeruginosa* biofilm antibiotic resistance," Nature, vol. 426, pp. 306-310, (2003).
Friedland et al., "Phenotypic antimicrobial resistance patterns in *Pseudomonas aeruginosa* and *Acinetobacter*: results of a Multicenter Intensive Care Unit Surveillance Study, 1995-2000," Diagnostic Microbiology and Infectious Disease, vol. 45, pp. 245-250, (2003).
Altschul, "A Protein Alignment Scoring System Sensitive at All Evolutionary Distances," J. Mol. Evol., vol. 36, pp. 290-300, (1993).
Altschul et al., "Basic Local Alignment Search Tool," J. Mol. Biol., vol. 215, pp. 403-410, (1990).
Todar, "*Pseudomonas aeruginosa*," Todar's Online Textbook of Bacteriology, http://textbookofbacteriology.net/pseudomonas.html, 12 pages, 2008.
Pirsi, "Phage therapy—advantages over antibiotics?" The Lancet, vol. 356, pp. 1418, (2000).
Bradbury, "My enemy's enemy is my friend," The Lancet, vol. 363, pp. 624-625, (2004).
Payne et al., "Pharmacokinetic Principles of Bacteriophage Therapy," Clinical Pharmacokinetics, vol. 42, pp. 315-325, (2003).
Murphy, "A Review of Techniques for the Investigation of Otitis Externa and Otitis Media," Clinical Techniques in Small Animal Practice, vol. 16, No. 3, pp. 236-241, (2001).

Ślopek et al., "Results of Bacteriophage Treatment of Suppurative Bacterial Infections III. Detailed Evaluation of the Results Obtained in Further 150 Cases," Archivum Immunologiae Et Therapiae Experimentalis, vol. 32, No. 317, pp. 317-335, (1984).

Eftekhar et al., "Alginase Treatment of Mucoid *Pseudomonas aeruginosa* Enhances Phagocytosis by Human Monocyte-Derived Macrophages," Infection and Immunity, vol. 56, No. 11, pp. 2788-2793, (1988).

Bayer et al., "Functional Role of Mucoid Exopolysaccharide (Alginate) in Antibiotic-Induced and Polymorphonuclear Leukocyte-Mediated Killing of *Pseudomonas aeruginosa*," Infection and Immunity, vol. 59, No. 1, pp. 302-308, (1991).

U.S. Appl. No. 12/897,741, mailed Sep. 27, 2011, Doc. No. R18, 12 Pages.

U.S. Appl. No. 13/333,684, mailed Apr. 10, 2012, Doc. No. R20, 37 Pages.

* cited by examiner

BENEFICIAL EFFECTS OF BACTERIOPHAGE TREATMENTS

FIELD OF THE INVENTION

The present invention relates to the sensitisation of previously resistant bacteria to antibiotics following treatment with bacteriophages. In particular, the invention provides in its preferred aspect for the preparation and administration of therapeutic medicaments that use sequential treatments with bacteriophages and conventional antibiotics, to be used with infections of animals and humans caused by pathogenic bacteria.

BACKGROUND TO THE INVENTION

Antibiotic resistance is now seen as one of the major challenges facing modern medicine. Given the shortage of novel antibiotics, a number of alternative approaches are being investigated, including the use of bacteriophages as therapeutic agents (Barrow & Soothill, Trends in Microbiology (1997), 5, 268-271; Dixon B, The Lancet Infectious Diseases (2004), 4, 186; Hausler T, Viruses vs. Superbugs: A Solution to the Antibiotics Crisis? (2006) MacMillan, New York; Matsuzaki et al, Journal of Infection and Chemotherapy (2005), 11, 211-219.

Bacteriophages (often known simply as "phages") are viruses that grow within bacteria. The name translates as "eaters of bacteria" and reflects the fact that as they grow most bacteriophages kill the bacterial host as the next generation of bacteriophages is released. Early work with bacteriophages was hindered by many factors, one of which was the widespread belief that there was only one type of bacteriophage, a non-specific virus that killed all bacteria. In fact, the host range of bacteriophages (the spectrum of bacteria they are capable of infecting) is often very specific. This specificity may be considered a therapeutic strength as populations of bacteriophages can be selected to specifically eliminate only the target bacterial species.

Despite the therapeutic advantages afforded by the host specificity of bacteriophages, this characteristic has the disadvantage that it can be difficult to achieve breadth of coverage of target strains. For this reason, there has been interest in finding combinations of bacteriophages having broad targeting capability in relation to particular types of bacterial infection (see for example Pirsi, The Lancet (2000) 355, 1418). This has now been achieved with the development of a mixture of six bacteriophages targeting *Pseudomonas aeruginosa*, which has completed veterinary field trials and is now in human clinical trials (Soothill et al, Lancet Infectious Diseases (2004) 4, 544-545). The challenge now is to develop regimens which optimise the delivery of such therapies.

Bacteriophages and antibiotic therapy have previously been used together in Eastern Europe (see for example Bradbury, The Lancet (February 2004) 363, 624-625), but without specific reporting of synergistic effects. Indeed, there have been suggestions that antibiotics can have adverse effects on use of bacteriophage therapy since bacteriophages use bacterial metabolism to replicate and this is inhibited by antibiotics (Payne and Janssen, Clinical Pharmacokinetics (2002) 42, 315-325).

More recently, bacteriophages have been shown to produce benefits where mixed pathogenic bacteria grow in a biofilm (Soothill et al, 2005, PCT patent application WO2005009451). In this application benefit was shown with respect to subsequent antibiotic treatment of heterologous bacterial infections, apparently by disruption of the biofilm following bacteriophage treatment.

Biofilm formation is now known to be a characteristic of many important pathogenic bacteria contributing to increased resistance to antibiotics. Such bio films may comprise more than one type of bacterium supported and surrounded by an excreted extracellular matrix and assist bacteria to colonize surfaces from marine reefs to tooth enamel. Biofilms allow bacteria to attach to surfaces and to attain population densities which would otherwise be unsupportable. They impart increased resistance to not only antibiotics but many environmental stresses including toxins such as heavy metals, bleaches and other cleaning agents. It was previously thought that contribution of biofilm formation to antibiotic resistance was primarily a physical process arising from limitation of diffusion, but more recent evidence has shown that some bio films appear to have specific abilities to trap antibiotics (Mah et al., Nature (2003) 426, 306-310). It is known that bacteria within biofilms can be 100 to 1000 times more resistant to antibiotics than the same strain of bacteria growing in single-celled ("planktonic") forms. This increased resistance means that bacteria that are apparently sensitive to antibiotics in a laboratory test may be resistant to therapy in a clinical setting. Even if some are cleared, biofilms may provide resistant reservoirs permitting rapid colonization once antibiotics are no longer present. It is clear therefore that biofilms are major factors in many human diseases.

As noted above, greater beneficial effects have been observed with the subsequent use of antibiotics against mixed infections following the use of a therapeutic bacteriophage preparation against *Pseudomonas aeruginosa*, and it has been proposed that this is due to the destruction of *Pseudomonas aeruginosa* as the key species maintaining the bio film (Soothill et al, 2005, PCT patent application WO2005009451), which results in loss of biofilm integrity and thus exposure of bacteria to conventional antibiotics.

The teaching of PCT patent application WO2005009451 is against the use of antibiotics that are specifically active against the same bacterial species as that targeted by bacteriophage. The examples cited refer to the use of Synulox (amoxicillin and clavulanic acid) and/or Canaural ear drops (containing diethanolamine fusidate, framycetin sulphate, nystatin and prednisolone). Both of these preparations contain only antibiotics that are not effective against *Pseudomonas aeruginosa* (Krogh et al, Nordisk Veterinaer Medicin (1975) 27, 285-295; Kucers A, in Kucers et al (eds), The Use of Antibiotics: A Clinical Review of Antibacterial, Antifungal and Antiviral Drugs, Fifth edition (1997), Butterworth-Heinemann, Oxford; Rawal, Journal of Antimicrobial Chemotherapy (1987) 20, 537-540). In particular, while aminoglycoside antibiotics as a class are effective against *Pseudomonas aeruginosa*, Framycetin is of very limited efficacy. Kucers notes that "Nearly all the medically important Gram-negative aerobic bacteria are sensitive" (to Neomycin, Framycetin and Paromomycin) "with the exception of *Pseudomonas aeruginosa*", while the same author states that "*Pseudomonas aeruginosa* is co-amoxiclav resistant, citing the work of Comber et al, in Rolinson & Watson Augmentin (eds) (1980), Excerpta Medica, Amsterdam, p. 19. Co-amoxiclav is defined in the online $52^{nd}$ edition of the British National Formulary (www.bnf.org) as "a mixture of amoxicillin (as the trihydrate or as the sodium salt) and clavulanic acid (as potassium clavulanate), equating to the veterinary drug Synulox. Thus, PCT patent application WO2005009451 would not indicate the use of antibiotics targeting *Pseudomonas* in any combination with bacteriophages but rather the use of antibiotics specifically targeting co-infecting bacteria.

Another mechanism has been identified recently by which bacteriophages can increase the sensitivity of bacteria to antibiotics to which they are resistant (Hagens et al, Microbial Drug Resistance (2006), 12, 164-168). This involves active bacteriophage metabolism, and is suggested to involve the formation of pores in the bacterial membrane. However, this teaches that "resensitization of pathogens resistant to a particular antibiotic can be achieved in the presence of phage in vivo" based around the use of "a combination treatment with antibiotics and filamentous phage". Thus this relates to a non-heritable characteristic which is exerted only in the presence of bacteriophage, which relies on the simultaneous use of both bacteriophages and antibiotics, and which appears to be specific to filamentous bacteriophages which form pores in the bacterial membrane. This is thus distinct from the inventions claimed herein, which induce heritable changes that persist even when actively replicating bacteriophage is not present.

SUMMARY OF THE INVENTION

The present invention is based on the induction of sensitivity to chemical antibiotics by the use of bacteriophage treatment in vivo in humans or in animals, where such sensitivity is heritable, does not rely on active bacteriophage metabolism and does not relate to the destruction of bio film to induce such sensitivity, along with the preparation of medicaments to permit the sequential use of bacteriophages and antibiotics so as to take advantage of such induction in sensitivity in the control of bacterial disease, especially for example a *Pseudomonas aeruginosa* infection. Induction of sensitivity in this context will be understood to include improvement of sensitivity.

DETAILED DESCRIPTION

Thus in one aspect, there is provided a bacteriophage preparation comprising one or more bacteriophages for use in combined bacteriophage and antibiotic therapy to treat a bacterial infection in a human or animal, wherein at least one antibiotic is administered following the start of said bacteriophage treatment at a time period at which susceptibility of bacterial cells of said infection to said antibiotic is induced or improved by the bacteriophage treatment, where such susceptibility is heritable, independent of continuing bacteriophage metabolism within those cells, and does not relate to the destruction of a biofilm to induce such sensitivity. Antibiotic sensitivity may be monitored by established procedures in vitro. Induction of sensitivity may be confirmed for one or more bacterial strains from the individual patient or may be identified in other patients with similar bacterial infections following bacteriophage treatment In a further aspect, there is provided a two stage medicament where the first stage comprises a bacteriophage-based therapeutic and the second is composed of one or more chemical antibiotics, for sequential use in humans or animals, where this is designed to exert beneficial effects by the induction of sensitivity as noted above.

The bacteriophage therapeutic and one or more chemical antibiotics may be administered for example at an interval of one to two days to two months apart, preferably at an interval of one to four weeks, most preferably at an interval of two weeks apart.

As indicated above, combined phage/antibiotic therapy according to the invention may be particularly useful for example in targeting bacterial infection comprising or consisting of *Pseudomonas aeruginosa*. Such infection may be, for example, at the site of a skin burn or other skin wound. It may be in the lung, an ocular infection or an ear infection. In this context, such an infection comprising *P. aeruginosa* will be understood to include an infection consisting essentially of *P. aeruginosa*. Thus, phage therapy according to the invention may be applied to an infection composed entirely, predominantly or significantly of *P. aeruginosa*.

EXAMPLES

Induction of Antibiotic Sensitivity in a Veterinary Field Trial

Canine ear infections caused by *Pseudomonas aeruginosa* (*otitis externa* and *otitis media*) are examples of clinical disease associated with biofilm-based colonization of a body surface. Clinical signs of such infection include pain, irritation (erythema), ulceration and the discharge of increased amounts of material from the ear. This is often purulent in nature and is accompanied by a distinctive odour.

A combined preparation of six bacteriophages was named BioVet-PA, and was authorized for trial in dogs with such infection by the Veterinary Medicines Directorate of the United Kingdom in November 2003.

Conduct of the Trial

BioVet-PA was stored at −80° C. Immediately prior to administration, the product was thawed and warmed in the hand. 0.2 ml (containing $1\times10^5$ infectious units of each of the 6 bacteriophages) was administered drop-wise using a sterile 1 ml capacity syringe into the ear. Ear condition and microbiology was assessed at 2 days post-administration.

The procedure was as follows:
Characterisation (2 to 14 days prior to treatment):
Day 0 Swabs taken from each ear by a veterinary surgeon
   Laboratory tests carried out using these swabs to confirm presence of *Pseudomonas aeruginosa*.
If *Pseudomonas aeruginosa* was not detected, the dog was excluded from the trial
Day 1 If *Pseudomonas aeruginosa* was detected, the isolates were tested for sensitivity to BioVet-PA.
If the *Pseudomonas aeruginosa* strain(s) with which the dog was infected was/were not sensitive to BioVet-PA, the dog was excluded from the trial.
Treatment:
Day 0 Ears examined auroscopically to assess their condition.
Swabs taken from each ear for microbiological analysis.
Dog's core temperature measured
Dog given dose of 0.2 ml BioVet-PA into the ear (treatments administered drop-wise using a sterile 1 ml-capacity syringe, and ear canals then massaged to promote deep penetration).
Day 2 Ears examined to assess their condition.
Swabs taken from each ear for microbiological analysis.
Dog's core temperature measured.
Only where both ears were infected:
Dog given dose of 0.2 ml BioVet-PA into the second ear (treatments administered drop-wise using a sterile 1 ml-capacity syringe, and ear canals then massaged to promote deep penetration).
Day 4 Only where both ears were infected:
Ears examined to assess their condition.
Swabs taken from each ear for microbiological analysis.
Dog's core temperature measured.
Results:
Studies on ten dogs with severe, antibiotic-resistant *Pseudomonas aeruginosa* ear infections treated with BioVet- PA showed improvement in clinical symptoms within two days of treatment and reductions in bacterial numbers over the same timescale. Bacteriophage replication was observed in all dogs. Analysis of the improvement in clinical symptoms showed this to be significant at the 95% level of confidence by both the t-test and the Wilcoxon matched-pairs test.

Three dogs were excluded from the trial. The first dog to be tested was excluded because of a subsequent change in the scoring system (to take account of ear discharge purulence) while two treated dogs proved to have infections that were not predominantly with the target bacterium at the time of treatment (due to a change in bacterial flora following pre-entry screening).

Antibiotic Resistance:

All isolates of *Pseudomonas aeruginosa* from all thirteen dogs that were collected before treatment were screened for their sensitivity to antibiotics. The antibiotic sensitivity profile of each *Pseudomonas aeruginosa* strain was assessed with a range of 10 antibiotics which may be used clinically by veterinarians to treat *Pseudomonas aeruginosa* infections. The results were recorded in appropriate data collection sheets.

Since differing colony types were often observed in the same dog and both ears were infected in four dogs, a total of 83 individual isolates of *Pseudomonas aeruginosa* were tested. Thus, 830 tests were carried out, of which 340 were on swabs taken immediately prior to treatment, 340 two days after treatment, and 150 four days after treatment.

All sensitivity assays were compared to identify shifts in sensitivity to any of the antibiotics tested. No individual isolate showed more than a single shift, and no isolate changed from fully sensitive to fully resistant, or fully resistant to fully sensitive. However, shifts from sensitive to partially resistant, partially resistant to resistant, resistant to partially resistant, or partially resistant to sensitive were seen for 16 isolates. Events were observed as shown in Table 1 below.

*Pseudomonas aeruginosa* shown to be susceptible to one or more of the bacteriophages present in BioPhage-PA.

This study investigated the efficacy and safety of BioPhage-PA, a mixture of six *Pseudomonas aeruginosa* bacteriophages of the same types as those tested as BioVet-PA in the veterinary field trial, which formed part of the pre-clinical work for this study.

The six bacteriophage strains (which were deposited at the National Collection of Industrial and Marine Bacteria, 23 St Machar Drive, Aberdeen, AB24 3RY, Scotland, UK on 24 Jun. 2003) are as follows:

| Reference | NCIMB Deposit Number |
|---|---|
| BC-BP-01 | NCIMB 41174 |
| BC-BP-02 | NCIMB 41175 |
| BC-BP-03 | NCIMB 41176 |
| BC-BP-04 | NCIMB 41177 |
| BC-BP-05 | NCIMB 41178 |
| BC-BP-06 | NCIMB 41179 |

These bacteriophages are effective at killing a broad range of *P. aeruginosa* isolates.

The study was carried out in two parallel groups of patients with ear infection caused by *Pseudomonas aeruginosa*. Patients were randomly allocated to receive a single dose of either BioPhage-PA or placebo and were monitored in a double-blind design over a period of 6 weeks post-dose. Efficacy assessments included questions about adverse events, both patients and investigator assessment of disease severity using visual analogue scales, *Pseudomonas aeruginosa* and bacteriophage ear swab count, audiogram, photography of the ear, and aural temperature analysis. Change from baseline (pre-dose assessment) in active and placebo groups were compared statistically. Safety data was also compared in the 2 groups.

TABLE 1

|  | Amikacin | Ceftazidime | Ciprofloxacin | Gentamicin | Aztreonam | Tobramycin | Meropenem | Piperacillin + Tazobactam | Colistin | Imipenem |
|---|---|---|---|---|---|---|---|---|---|---|
|  |  |  |  |  |  |  |  | All sensitive |  |  |
| Sensitive change to Partially resistant |  |  |  |  |  | 1 |  |  |  |  |
| Partially resistant change to Resistant |  |  |  | 1 |  |  |  |  |  |  |
| Resistant change to Partially resistant | 6 |  | 3 | 5 |  |  |  |  |  |  |
| Partially resistant change to Sensitive | 2 |  | 2 | 5 |  | 5 |  |  |  |  |
| Monitored isolates in total |  |  |  |  | 340 |  |  | 100% |  |  |
| more resistant |  |  |  |  | 2 |  |  | 0.59% |  |  |
| more sensitive |  |  |  |  | 28 |  |  | 8.24% |  |  |

A total of 30 alterations in antibiotic sensitivity were seen, with 28 being shifts towards sensitivity and 2 being shifts towards resistance. Thus shifts towards sensitivity outnumbered those towards resistance by a factor of 14:1, illustrating the predominance of such "beneficial" shifts following bacteriophage treatment.

Induction of Antibiotic Sensitivity in a Human Clinical Trial:

The trial was a single-centre, double-blind, randomised, parallel group study of the safety and efficacy of a single administration of BioPhage-PA (a mixture of six bacteriophages specific for *Pseudomonas aeruginosa*) compared with placebo in patients with chronic ear infection caused by Study Design This was a single-centre, double-blind, randomised, parallel group study in patients with chronic *Pseudomonas aeruginosa* infection of the ear. Patients were randomised to one of two groups:

Group 1:

Patients received a single 0.2 mL dose of BioPhage-PA (containing $1 \times 10^5$ pfu by original titration of each of the 6 therapeutic bacteriophages)

Group 2:

Patients received a single 0.2 mL dose of placebo (10% v/v glycerol in PBS)

Design Summary

Pre-Study Visit

Patients attended the clinic within 2 weeks of treatment Day 0 after being informed of the trial verbally. At this visit, they were provided with a written information sheet and were also provided with study details verbally. Patients were questioned regarding their eligibility to participate and if successful signed a consent form prior to Day 0 of the trial.

Treatment Period (Days 0-42 Inclusive)

Patients attended the clinic on the morning of Day 0 for clinical examination and were questioned about adverse events and study compliance. Upon confirmation of eligibility, patients were randomised to one of the two treatment groups and had baseline assessments performed to determine the severity of the infection. Treatment was then administered by the clinician who instilled the therapy drop-wise into the ear. Patients remained in the clinic for 6 hours post-dose. They were issued with diary cards for recording any adverse events or comments on the condition of the ear on a daily basis whilst away from the unit.

Patients returned on Days 7, 21 and 42 for further safety and efficacy tests.

A patient was eligible for inclusion in this study only if all of the following criteria apply: Aged 18 or over; able and willing to give written informed consent to take part in the study; infection of a the ear shown to be caused predominantly or solely by *Pseudomonas aeruginosa*; *Pseudomonas aeruginosa* isolated from the infection and shown to be vulnerable to one or more of the bacteriophages present in BioPhage-PA; infection established for at least 6 weeks and proven unresponsive to conventional anti-bacterial therapy; available to attend all clinic visits and complete all study measurements; female patients to be postmenopausal, surgically sterile or willing to use an acceptable form of contraception.

A patient was not eligible for inclusion in this study if any of the following criteria applied: Local surgery within 3 months of the pre-study visit; acute or systemic sepsis; use of systemic or topical antibiotics within one week of the pre-study visit or during the study; use of topical antiseptic or anti-inflammatory agents within one week of the pre-study visit or during the study; bacteriophage therapy in the 6 months prior to the pre-study visit; hemolytic Streptococci of groups A, B, C and G or unusual bacterial or fungal flora on ear swab culture at the pre-study visit; female pregnant or intending to become pregnant; patients who have a past or present disease which, as judged by the investigator, may affect the outcome of the study; any other condition which the investigator feels may prejudice the results of the study; participation in another clinical trial involving a new molecular entity within the previous 4 months or any trial within the previous one month.

Study Assessments and Procedures

Each patient attended the unit for the following visits:

Prior to the official start of the study, swabs (in transport media) were taken from the ears of potential trial candidates. General microbiological analysis was carried out to determine the level of *Pseudomonas aeruginosa* in the ear. This was followed by a diagnostic ear-swab test. The trial was discussed verbally with patient, and the patient was provided with information sheet/consent form; history was taken and recorded on the case report form; a diagnostic swab was taken and the swab sent for microbiological analysis, where it was analysed for *Pseudomonas aeruginosa* and for sensitivity of *Pseudomonas aeruginosa* that was present to the bacteriophages in BioPhage-PA.

If suitable, the patient was enrolled onto trial within 2 weeks of the time that the diagnostic swab was taken.

Study Day 0: The patient assessed the condition of their ear for: discomfort, itchiness, wetness, and smell. Using pre-weighed dry swabs, samples were taken for microbiological analysis. Oral and aural temperature were recorded, the ear was cleaned, and the attending physician assessed the ear for: erythema/inflammation, ulceration/granulation/polyps, discharge type (clear/mucoid/mucopurulent), discharge quantity, and odour (immediately prior to study procedures). Digital otoscopic photography was performed, along with a hearing test (audiogram). BioPhage-PA (0.2 ml) was then administered directly into the ear canal using a 1 ml syringe and soft sterile tubing over a period of approximately 30 seconds. The patient remained at the clinic for 6 hours after therapy for observation and was then sent home with a diary card to record any information they felt relevant to their condition.

Study Day 7: This involved adverse event and compliance questioning, patient assessment of the ear, swab sampling with microbiological analysis, recording of aural and oral temperature, physician assessment of the ear, and ear cleaning.

Study Day 21: This involved procedures as described for study day 7

Study Day 42: This involved procedures as described for study days 7 and 21, except that a hearing test was also be performed and the ear was photographed.

Microbiological Assessment

Microbiological assessment involved counting of the *Pseudomonas aeruginosa* present on the swab, along with counting of all bacteriophages (both extraneous and therapeutic) on the swab.

Sensitivity to ten antibiotics (as for the veterinary field trial) was also monitored for all isolates. The antibiotic sensitivity test was conducted on each strain of *Pseudomonas aeruginosa* isolated. The test was conducted according to the standard methods of the British Society for Antimicrobial Chemotherapy (BSAC) Disc Diffusion Method for Antimicrobial Susceptibility Testing (May 2003). The antibiotics to be used were as follows:

Amikacin—30 µg/ml
Ceftazadime—30 µg/ml
Ciprofloxacin—5 µg/ml
Gentamicin—10 µg/ml
Meropenem—10 µg/ml
Pipericillin+Tazobactam (7.5:1)—85 µg/ml
Colistin—25 µg/ml
Aztreonam—30 µg/ml
Imipenem—10 µg/ml
Tobramycin—10 µg/ml The test was conducted using Isosensitest agar.

It was found that in the first patient in which bacteriophage replication was seen, there was evidence of a movement towards sensitivity for three of the ten antibiotics monitored (see Table 2).

TABLE 2

Antibiotic sensitivity of *Pseudomonas aeruginosa*:
Data from human otitis trial

| Antibiotic | Pre-treatment screening | Day 0 (treatment) | Day 7 | Day 21 | Day 42 |
|---|---|---|---|---|---|
| Amikacin | Partially resistant | Partially resistant | Sensitive | Partially resistant | Sensitive |
| Gentamicin | Resistant | Resistant | Resistant | Resistant | Partially resistant |
| Tobramycin | Resistant | Sensitive | Resistant | Partially resistant | Resistant |
| Meropenem | Sensitive | Sensitive | Sensitive | Sensitive | Sensitive |
| Imipenem | Sensitive | Sensitive | Sensitive | Sensitive | Sensitive |
| Ceftazadime | Sensitive | Sensitive | Sensitive | Sensitive | Sensitive |
| Pipericillin & Tazobactam | Sensitive | Sensitive | Sensitive | Sensitive | Sensitive |
| Colistin | Sensitive | Sensitive | Sensitive | Sensitive | Sensitive |
| Aztreonam | Sensitive | Sensitive | Sensitive | Sensitive | Sensitive |
| Ciprofloxacin | Sensitive | Sensitive | Sensitive | Sensitive | Sensitive |

Summary of the Above Exemplification

In the veterinary field trial, over a two to four day monitoring period, evidence was found of a movement towards antibiotic sensitivity in 8.24% of *Pseudomonas aeruginosa* isolates (against 0.59% where movement towards resistance was seen).

In human trial, evidence was seen of a movement towards sensitivity to chemical antibiotics following the use of a bacteriophage therapeutic in the first patient where bacteriophage replication was observed. Such movement was seen for three of ten antibiotics monitored (30%), over the longer monitoring period in this trial.

Further Human Trial Results

Subsequent analysis of all twenty four participants in the human trial confirmed the above findings as follows with reference to Tables 3 and 4 below. It can be seen that cessation of antibiotic treatment (required for trial entry) itself produced a drift towards antibiotic sensitivity, but that this was more marked for both numbers of patients and for individual antibiotics assayed in the test (bacteriophage-treated) group, with the majority of patients (7/12) showing at least one change towards sensitivity during the monitoring period. Shifts to sensitivity appear particularly marked for aminoglycoside antibiotics with, for example, five of twelve bacteriophage-treated patients showing increased sensitivity to gentamicin. Taken together, the above data exemplifies the present invention.

TABLE 3

Antibiotic sensitivity of *Pseudomonas aeruginosa*:
Data from human otitis trial
Change from pre-screening to day 42

Placebo group

| Antibiotic | 3 | 4 | 6 | 8 | 9 | 11 | 13 | 14 | 19 | 20 | 22 | 23 |
|---|---|---|---|---|---|---|---|---|---|---|---|---|
| Amikacin | | | | | | | + | + | | | | |
| Gentamicin | | | | | | | + | − | | + | | |
| Tobramycin | | | | | | | | + | + | | | |
| Meropenem | | | | | | | | | | | | |
| Imipenem | | | | | | | | | | | | |
| Ceftazadime | | | | | | | | | | | | |
| Pipericillin & Tazobactam | | | | | | | | | | | | |
| Colistin | | | | | | | | | | | | |
| Aztreonam | | | | | | + | | | | | | |
| Ciprofloxacin | | | | | | | | | | | | |

TABLE 3-continued

Antibiotic sensitivity of *Pseudomonas aeruginosa*:
Data from human otitis trial
Change from pre-screening to day 42

Test group

| Antibiotic | 1 | 2 | 5 | 7 | 10 | 12 | 15 | 16 | 17 | 18 | 21 | 24 |
|---|---|---|---|---|---|---|---|---|---|---|---|---|
| Amikacin | + | − | | | | | + | | | | | + |
| Gentamicin | + | + | | | | | + | + | | | | + |
| Tobramycin | | − | | − | | | | | | | | + |
| Meropenem | | | | | | | | | | | | |
| Imipenem | | | | | | | | | | | | |
| Ceftazadime | | | | | | | | | | | | |
| Pipericillin & Tazobactam | | | | | | | | | | | | |
| Colistin | | | | | | | | | | | | |
| Aztreonam | | | | | | | | | | | | + |
| Ciprofloxacin | | | | | | + | | | | | | |

TABLE 4

Changes in resistance patterns:

| | | | Antibiotic (ten drugs tested) | | | |
|---|---|---|---|---|---|---|
| | | | To resistance | | To sensitivity | |
| | | n = | No. | % | No. | % |
| Test | | | | | | |
| Patients (one or more changes) | of | 12 | 2 | 16.7% | 7 | 58.3% |
| Individual tests | of | 120 | 3 | 2.5% | 11 | 9.2% |
| Control | | | | | | |
| Patients (one or more changes) | of | 12 | 1 | 8.3% | 5 | 41.7% |
| Individual tests | of | 120 | 1 | 0.8% | 7 | 5.8% |

The invention claimed is:

1. A method to induce sensitivity to chemical antibiotics in bacterial cells, comprising administering one or more bacteriophages in vivo in a human or animal; and monitoring induction of the sensitivity by antibiotic sensitivity testing in vitro, both before and after the administering of the one or more bacteriophages;

where the sensitivity is heritable, independent of continuing bacteriophage metabolism within those cells, and does not relate to the destruction of a biofilm to induce sensitivity, and the bacterial cells are *Pseudomonas aeruginosa*.

2. The method of claim 1 where testing is used to select chemical antibiotics for therapeutic use in a patient.

3. The method of claim 1 where there is induction of sensitivity to an aminoglycoside antibiotic.

4. The method according to claim 1 wherein the one or more bacteriophages comprises a combined preparation of six bacteriophages NCIMB (National collection of Industrial and Marine Bacteria) 41174, NCIMB 41175, NCIMB 41176, NCIMB 41177, NCIMB 41178 and NCIMB 41179.

5. The method according to claim 1 further comprising administering at least one antibiotic.

6. A method to induce or improve susceptibility to an antibiotic in bacterial cells comprising:
 administering to a human or animal with a bacterial infection, a bacteriophage preparation comprising one or more bacteriophages, and
 determining the ability of said preparation to increase susceptibility of said cells to said antibiotic by in vitro antibiotic testing in the absence of bacteriophages using samples of bacterial cells from said infection or from another infection by the same or a comparable bacterial strain of the same species subject to identical exposure to said bacteriophage preparation,
 wherein said in vitro antibiotic testing is carried out both before and after the exposure to said bacteriophage preparation, and
 said infection is a *Pseudomonas aeruginosa* infection.

7. The method according to claim 6 wherein said one or more bacteriophages induce or improve susceptibility to an aminoglycoside antibiotic.

8. The method according to claim 6 where the testing is used to select chemical antibiotics for therapeutic use in a patient.

9. The method according to claim 6 further comprising administering at least one antibiotic.

10. The method according to claim 6 where the one or more bacteriophages comprises a combined preparation of six bacteriophages NCIMB (National collection of Industrial and Marine Bacteria) 41174, NCIMB 41175, NCIMB 41176, NCIMB 41177, NCIMB 41178 and NCIMB 41179.

11. A method to treat a bacterial infection in a human or animal, comprising:
 testing bacteria from the bacterial infection for susceptibility to an antibiotic, before the bacteria are exposed to a bacteriophage preparation,
 administering the bacteriophage preparation to the human or animal, to expose the bacteria in the bacterial infection, to the bacteriophage preparation,
 testing the bacteria from the bacterial infection for susceptibility to the antibiotic, after the bacteria are exposed to the bacteriophage preparation, and
 administering the antibiotic to the human or animal, after administering the bacteriophage preparation,
 wherein the bacteriophage preparation comprises one or more bacteriophages,
 susceptibility of the bacteria to the antibiotic after the bacteria are exposed to the bacteriophage preparation, is greater than susceptibility of the bacteria to the antibiotic before the bacteria are exposed to the bacteriophage preparation, and
 the bacteria are *Pseudomonas aeruginosa*.

12. The method according to claim 11 wherein a time period between administering the bacteriophage preparation and administering the antibiotic is one to two days.

13. The method according to claim 11 wherein said infection is a *Pseudomonas aeruginosa* infection.

14. The method according to claim 13 where the one or more bacteriophages comprises a combined bacteriophage preparation of six bacteriophages NCIMB 41174, NCIMB 41175, NCIMB 41176, NCIMB 41177, NCIMB 41178 and NCIMB 41179.

15. The method according to claim 11 wherein a time period between administering the bacteriophage preparation and administering the antibiotic is one day to two months.

16. The method according to claim 11, wherein the antibiotic is an aminoglycoside antibiotic.

* * * * *

UNITED STATES PATENT AND TRADEMARK OFFICE
CERTIFICATE OF CORRECTION

PATENT NO. : 8,475,787 B2
APPLICATION NO. : 12/529876
DATED : July 2, 2013
INVENTOR(S) : David Harper Page 1 of 1

It is certified that error appears in the above-identified patent and that said Letters Patent is hereby corrected as shown below:

On the Title Page, Item (56)

Other Publications, Page 1
Col. 2, line 3, delete "*Pseudomgnas*" and insert --*Pseudomonas*--.

Signed and Sealed this
Fifth Day of November, 2013

Teresa Stanek Rea
*Deputy Director of the United States Patent and Trademark Office*

UNITED STATES PATENT AND TRADEMARK OFFICE
CERTIFICATE OF CORRECTION

PATENT NO. : 8,475,787 B2  Page 1 of 1
APPLICATION NO. : 12/529876
DATED : July 2, 2013
INVENTOR(S) : David Harper It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 484 days.

Signed and Sealed this

Eighth Day of September, 2015

Michelle K. Lee
*Director of the United States Patent and Trademark Office*